(12) United States Patent
Widzgowski

(10) Patent No.: US 10,824,116 B2
(45) Date of Patent: Nov. 3, 2020

(54) METHOD FOR FORMING A DIGITAL VALUE FROM A CLOCK SIGNAL AND FROM A DATA SIGNAL

(71) Applicant: Leica Microsystems CMS GmbH, Wetzlar (DE)

(72) Inventor: Bernd Widzgowski, Dossenheim (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 0 days.

(21) Appl. No.: 16/498,393

(22) PCT Filed: Apr. 4, 2018

(86) PCT No.: PCT/EP2018/058523
§ 371 (c)(1),
(2) Date: Sep. 27, 2019

(87) PCT Pub. No.: WO2018/185121
PCT Pub. Date: Oct. 11, 2018

(65) Prior Publication Data
US 2020/0041961 A1 Feb. 6, 2020

(30) Foreign Application Priority Data
Apr. 7, 2017 (DE) .................. 10 2017 107 560

(51) Int. Cl.
*G04F 10/00* (2006.01)
*G16H 10/40* (2018.01)
(Continued)

(52) U.S. Cl.
CPC ....... *G04F 10/005* (2013.01); *G02B 21/0084* (2013.01); *G16H 10/40* (2018.01); *H04L 7/033* (2013.01)

(58) Field of Classification Search
CPC .. G04F 10/005; G16H 10/40; G02B 21/0084; H04L 7/033
(Continued)

(56) References Cited

U.S. PATENT DOCUMENTS

2005/0081245 A1* 4/2005 Arad ................. H04N 21/4383
725/100
2012/0112817 A1* 5/2012 Guedon ............... H03M 3/356
327/517
(Continued)

FOREIGN PATENT DOCUMENTS

WO WO 2006067716 A2 6/2006
WO WO 2016040884 A1 3/2016

OTHER PUBLICATIONS

Kubicek, Michel et al. "Blind Oversampling Data Recovery with Low Hardware Complexity,"Radioengineering, Apr. 1, 2010, pp. 74-78, XP055488892.
(Continued)

*Primary Examiner* — Lam T Mai
(74) *Attorney, Agent, or Firm* — Leydig, Voit & Mayer, Ltd.

(57) ABSTRACT

A method forms a digital value from a clock signal and a digital data signal. The method includes sampling the clock signal in order to obtain a clock signal digital value sequence and sampling the digital data signal in order to obtain a data signal digital value sequence. Sampling points are ascertained from the clock signal digital value sequence, at which data signal digital values are extracted from the data signal digital value sequence. The digital value is formed from the data signal digital values.

12 Claims, 3 Drawing Sheets

(51) Int. Cl.
*G02B 21/00* (2006.01)
*H04L 7/033* (2006.01)

(58) Field of Classification Search
USPC .................................................. 341/155–165
See application file for complete search history.

(56) References Cited

U.S. PATENT DOCUMENTS

| | | | |
|---|---|---|---|
| 2014/0375367 A1* | 12/2014 | Chen ...................... | H03K 3/017 |
| | | | 327/210 |
| 2015/0032300 A1* | 1/2015 | Arethens ................ | G01O 21/10 |
| | | | 701/17 |
| 2017/0347001 A1* | 11/2017 | Ghofrani ................ | A61B 3/102 |
| 2018/0313895 A1* | 11/2018 | Liang ............... | G01R 31/31709 |

OTHER PUBLICATIONS

Hsieh, Ming-ta et al. "Architectures for Multi-Gigabit Wire-Linked Clock and Data Recovery," IEEE Circuits and Systems Magazine, IEEE Service Center, New York, NY, US, Bd. 8, Nr. 4, Oct. 1, 2008, pp. 45-57, XP011235829.

Ahmed, S.I. et al. "Overview of Oversampling Clock and Data Recovery Circuits," Electrical and Computer Engineering, 2005. Canadian Conference on Saskatoon, SK, Canada, May 1-4, 2005, IEEE, Piscataway, NJ, USA, May 1, 2005, pp. 1876-1881, XP010869208.

Defossez, Marc, "An Interface for Texas Instruments Analog-to-Digital Converters with Serial LVDS Outputs," Apr. 7, 2008, XP055488504.

\* cited by examiner

METHOD FOR FORMING A DIGITAL VALUE FROM A CLOCK SIGNAL AND FROM A DATA SIGNAL

CROSS-REFERENCE TO PRIOR APPLICATIONS

This application is a U.S. National Phase Application under 35 U.S.C. § 371 of International Application No. PCT/EP2018/058523, filed on Apr. 4, 2018, and claims benefit to German Patent Application No. DE 10 2017 107 560.7, filed on Apr. 7, 2017. The International Application was published in German on Oct. 11, 2018 as WO 2018/185121 A1 under PCT Article 21(2).

FIELD

The present invention relates to a method for forming a digital value from a clock signal and a digital data signal, and a computing unit for carrying out said method.

BACKGROUND

In microscopy, for example, confocal microscopy, numerous sensors are used, of which the analog output signals must be digitized for further processing. For this purpose, widely used analog-digital converters (ADCs) may be used which, for example, are available as complete modules. In order in particular to design the cabling in a simple manner, analog-digital converters with serial output are frequently used, in which the digital values are output as a bit stream by means of a few lines (for example, bit clock, data, and frame). The further processing of the bit stream may take place in conventional integrated circuits (ICs) or field-programmable gate arrays (FPGAs), wherein the methods therefor are widely known and are already prepared in conventional modules, for example, the Virtex or Kintex FPGAs from Xilinx or the like.

However, when simultaneously evaluating numerous bit streams of different ADCs, as is the case in particular in confocal microscopy with its numerous photosensors, problems may be encountered in particular with respect to the timing. On the one hand, in the case of the known evaluation methods, in particular the clock signal (bit clock) and the data signal (data) must be resynchronized, as the signal processing initially results in a phase shift (see, for example, "Bit-Clock Alignment" in Xilinx, Application Note: Virtex-4 and Virtex-5 FPGAs, XAPP866 (v3.0) Apr. 7, 2008). On the other hand, this problem is exacerbated if multiple ADCs are involved which are situated at varying distances from the module.

SUMMARY

In an embodiment, the present invention provides a method for forming a digital value from a clock signal and a digital data signal. The method includes sampling the clock signal in order to obtain a clock signal digital value sequence and sampling the digital data signal in order to obtain a data signal digital value sequence. Sampling points are ascertained from the clock signal digital value sequence, at which data signal digital values are extracted from the data signal digital value sequence. The digital value is formed from the data signal digital values.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
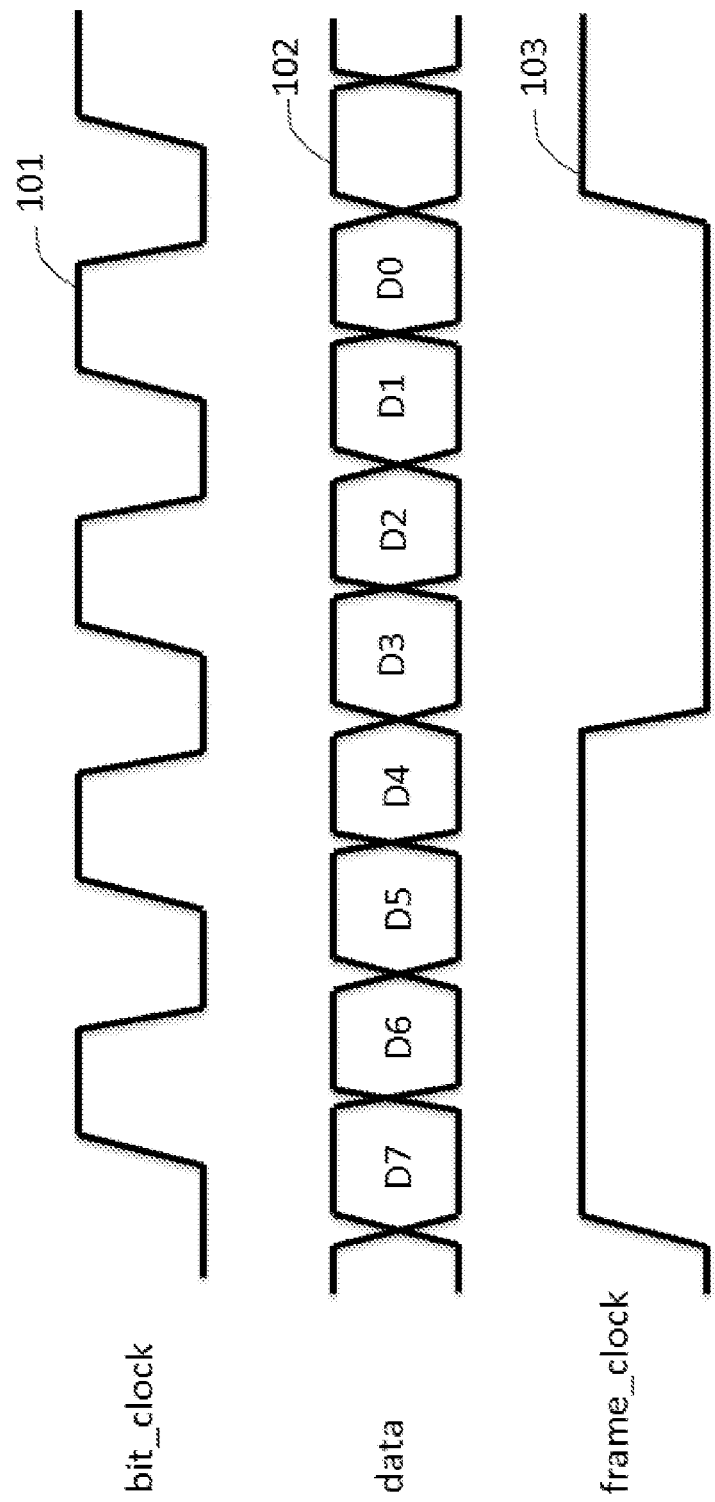
FIG. 1 schematically depicts typical signals as they are output by an ADC with serial output.

According to embodiments of the present invention, a method for forming a digital value from a clock signal and a digital data signal, and a computing unit for carrying out said method, are provided.

An embodiment of the present invention carries out the digital value formation in the evaluation module (IC or FPGA) not by means of conventional methods which are encumbered with the aforementioned problems, but rather using ("simple") signal sampling which is also prepared in the aforementioned modules and is possible at a very high sampling rate in the GHz range. In this way, digital signal value sequences are generated from the signals which are output by the ADC (at least the clock signal and data signal) and processed. Since the sampling of the various signals essentially takes place simultaneously, there is no phase shift between signals or other timing problems. Thus, by means of the present invention, a method is provided for forming a digital value in particular from the output signals of an ADC with serial output, which is robust, accurate, and easy to implement.

Preferably, the sampling instants are determined from value changes in the clock signal digital value sequence. The determination of sampling points at which the data signal has the required values for the further processing may in fact take place in a very simple manner by analyzing the clock signal. Sampling points are normally on the edges of the clock signal or are (preferably centered) between the edges. The specific relationship between suitable sampling points and edges is described in the data sheet of the ADC which is used. Thus, unlike in the prior art, no complex measures are necessary, for example, providing state machines and delay elements which are activated by them.

Advantageously, the clock signal digital value sequence is a binary value sequence, i.e., a value sequence having two values (typically "0" and "1"). As a result, the sampling and computation complexity may be reduced without negatively affecting the evaluation.

According to a preferred embodiment, the clock signal and/or the digital data signal are oversampled. Preferably, the sampling frequency is eight times or 16 times the frequency of the clock signal. In the case of oversampling of the clock signal, it is possible to determine in particular the edges of said clock signal, which are typically definitive for the sampling point of the data signal, in a manner which is particularly accurate with respect to time. In the case of oversampling the data signal, preferably at the same sampling rate as the clock signal, a sufficiently large number of data signal digital values are available which are also sampled precisely or approximately precisely at the sampling points as a function of the sampling rate, so that they may also be selected in a simple manner for forming the digital value. In principle, however, it is sufficient if the data signal is sampled only at the sampling points if they are known early enough.

Preferably, the data signal digital value sequence is a binary value sequence. Since a data signal which originates from a conventional ADC with serial output is a binary signal, it is also sufficient to implement the data signal digital value sequence as a binary signal sequence. As a result, the sampling and computation complexity may be reduced without negatively affecting the evaluation.

A particularly preferable possibility for forming the digital value comprises the data signal digital values forming the bits of the digital value. Thus, only simple operations are required for forming the digital value.

Since conventional ADCs generally also output a frame signal (frame clock), according to one refinement of the present invention, said frame signal is preferably also sampled. The resulting frame signal digital value sequence may then advantageously also be used to form the digital value. For example, the frame signal may indicate which bits from the data signal are associated with the same digital value. For example, each period of the frame signal corresponds to a digital value.

If desired, signals and/or signal digital value sequences may be filtered in order to remove interference. In particular, low-pass filters may be used to filter out noise and the like.

A computing unit according to the present invention, for example, an integrated circuit (IC) or an FPGA, in particular in a control unit of a microscope, is configured to carry out a method according to the present invention.

The present invention may advantageously be used in microscopy, in particular confocal microscopy, since numerous signals, for example, from photomultipliers, arrays of avalanche photodiodes (silicon photomultipliers, SiPMs), photodiodes, the analog output of a lock-in amplifier, or an analog signal which is generated by the user from said user's measurement equipment and which is to be recorded synchronously with the image, are to be detected there, preferably simultaneously, since, in the resulting images generated, the state of the sensors must be depicted at a pixel position at the same instant. If several images are recorded in succession, the image sequence mirrors temporal changes in the sample. The temporal correlation is thus necessary with all time-variant samples.

Additional advantages and embodiments of the present invention result from the description and the attached drawing.

It is to be understood that the aforementioned features and the features to be explained hereinafter are applicable not only in the respective specified combination, but also in other combinations or alone, according to different embodiments of the present invention.

FIG. 1 schematically depicts three typical signals which are output by an ADC with serial output. In particular, a clock signal (bit_clock) 101, a data signal (data) 102, and a frame signal (frame_clock) 103 are depicted.

The clock signal 101 designates the clock frequency of the signals and is used in particular for identifying the bits in the data signal 102. In the depicted embodiment, in particular each rising and falling edge in the clock signal designates one bit in the data signal. Thus, it is a so-called DDR (double data rate) signal. The frame signal 103 is used for designating the bits which are associated with the same digital value. In the present example, eight exemplary bits of a digital value (byte) in the data signal are designated by D0 to D7. Generally, however, more than 8 bits, by extension, for example, 10, 12 or 16 bits, may be associated with a digital value. Depending on the specific value (for example, "0" or "1"), the signal level for every bit is "high" or "low."

Figure 2:
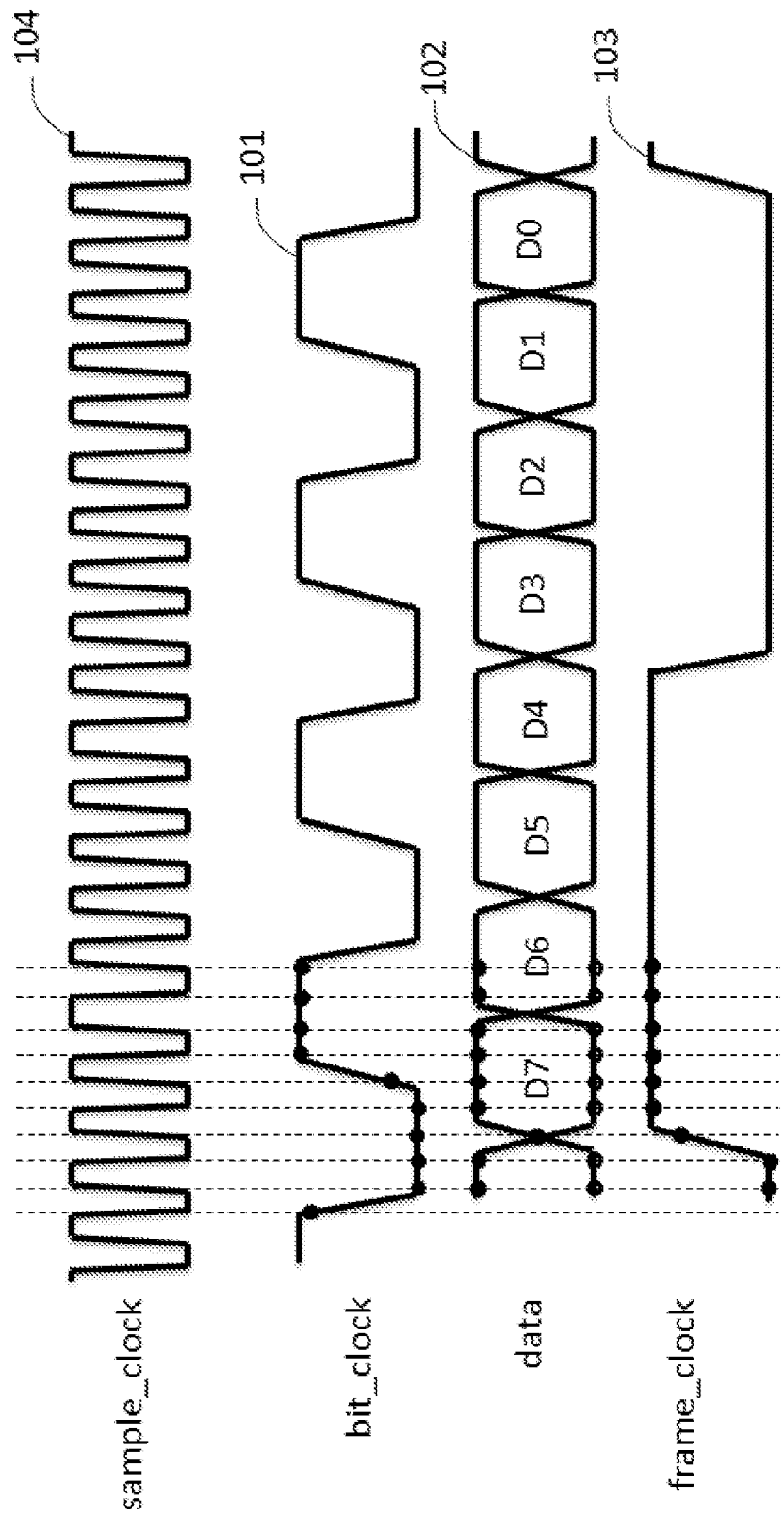
FIG. 2 schematically depicts the sampling of the signals from FIG. 1 according to a preferred embodiment of the present invention.
Figure 3:
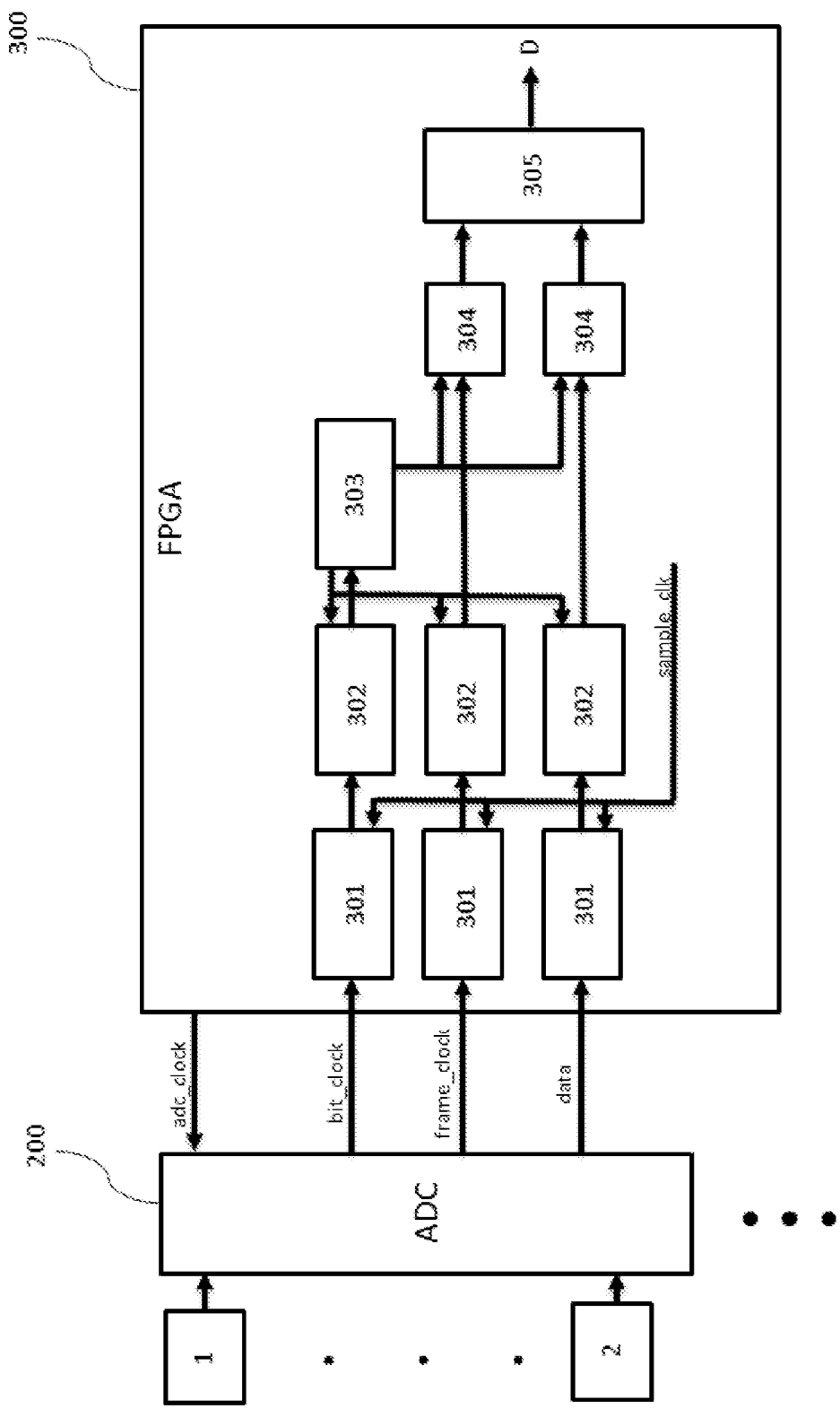
FIG. 3 schematically depicts a preferred embodiment of a computing unit according to the present invention.

With reference to FIGS. 2 and 3, a preferred embodiment of the present invention is described below, wherein FIG. 2 schematically depicts the sampling of the signals from FIG. 1, and FIG. 3 schematically depicts a preferred embodiment of a computing unit according to the present invention.

FIG. 3 schematically depicts an exemplary arrangement made up of a computing unit 300 according to a preferred embodiment of the present invention, one or several analog-digital converters 200 (ADCs) with serial output, which are connected to said arithmetic unit, and sensors 1, 2, . . . which are respectively connected to one of the one or the several ADCs 200. Such an arrangement may advantageously be used particularly in measuring devices which must detect numerous analog signals simultaneously, in particular confocal microscopes.

The sensors 1, 2, . . . may be any arbitrary sensors; in confocal microscopes, for example, photodetectors. The ADCs 200 may be conventional, in particular multichannel, analog-digital converters with serial output. The computing unit 200 is, for example, a conventional FPGA (field-programmable gate array).

The signals provided by the ADC 200 are routed to the FPGA 300 and sampled as depicted in FIG. 2, by means of sampling elements 301 of which the sampling rate in particular is adjustable.

FIG. 2 depicts the data signal 102, the clock signal 101, and the frame signal 103 being sampled in order to obtain corresponding signal digital value sequences. For example, a sampling rate is specified by a sampling clock signal 104 (sample_clock). For example, the sampling takes place at a rising edge as well as at a falling edge of the sampling clock signal 104, wherein the resulting measured values in the signals 101 to 103 are indicated by filled-in or open circles. It is apparent that in the depicted example, the signals 101 to 103 are oversampled, wherein the sampling frequency is approximately 4.5 to 5 times the frequency of the clock signal 101.

To simplify the evaluation and further processing, binary value sequences which have only the values "0" and "1" are used as a signal digital value sequences. For this purpose, in particular so-called deserializers are suitable as sampling elements 301. It is made up, for example, of an arrangement of flip-flops which are interconnected in a particular manner. Advantageously, only threshold value switches are situated at the associated inputs of the FPGA, in order to distinguish between the voltage levels which represent the logical signals.

In the depicted example, the clock signal digital value sequence thus consists of 1000001111 . . . , the data signal digital value sequence, for example, consists of 1111111111 . . . (filled-in circles), and the frame signal digital value sequence consists of 0011111111 . . . , thus:

| Position | 1 | 2 | 3 | 4 | 5 | 6 | 7 | 8 | 9 | 10 | |
|---|---|---|---|---|---|---|---|---|---|---|---|
| bit_clock | 1 | 0 | 0 | 0 | 0 | 0 | 1 | 1 | 1 | 1 | ... |
| data | 1 | 1 | 1 | 1 | 1 | 1 | 1 | 1 | 1 | 1 | ... |
| frame_clock | 0 | 0 | 1 | 1 | 1 | 1 | 1 | 1 | 1 | 1 | ... |

The signal digital value sequences are routed to storage elements 302, for example, so-called barrel shifters. The storage elements 302 are used for temporary storage and the targeted relaying of portions of the signal digital value sequences, in order to be able to process them further. The width of each of the storage elements 302 must be sized in such a way that at least one period of the clock signal 101 is stored, here, at least 9 to 10 bits. Advantageously, each of the storage elements 302 is sized in such a way that two periods of this clock signal fit in. This simplifies finding level changes.

Each buffered partial clock signal digital value sequence is routed to an evaluation element 303 which examines the partial clock signal digital value sequence for value changes. In the example above, a value change from 1 to 0 from the first to the second position, and from 0 to 1 from the sixth to the seventh position, are detectable. These value changes are understood to be edges in the clock signal 101. Having knowledge about the ADCs used, for example, the fourth position may thereby be ascertained as a suitable sampling point for the data signal 102. This information is transmitted to extraction elements 304 which extract the relevant bits from the partial data signal digital value sequence and the partial frame signal digital value sequence and route them to a digital value formation element 305.

If several different ADCs 200 are connected to the FPGA 300, the respective distances between the ADC and the FPGA are also normally different, so that the signals of the various ADCs 200 exist having different phase relationships. In such a case, the storage elements 302 or special delay elements may be used to synchronize the phases, i.e., to delay signals arriving earlier, until they are preferably in phase with signals arriving later.

Furthermore, the evaluation element 303 causes the relaying of a new partial clock signal digital value sequence, partial data signal digital value sequence, and partial frame signal digital value sequence from the storage elements 302, as a function of the progress of the evaluation.

After a sufficiently large number of steps, all information (here, bits) required for forming the digital value D is then present in the digital value formation element 305, and the digital value D is formed.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for forming a digital value from a clock signal and a digital data signal, the method comprising:
   sampling the clock signal in order to obtain a clock signal digital value sequence,
   sampling the digital data signal in order to obtain a data signal digital value sequence,
   ascertaining sampling points from the clock signal digital value sequence, at which data signal digital values are extracted from the data signal digital value sequence, and
   forming the digital value from the data signal digital values.

2. The method as claimed in claim 1, wherein the sampling points are determined from value changes in the clock signal digital value sequence.

3. The method as claimed in claim 1, wherein the clock signal digital value sequence is a binary value sequence.

4. The method as claimed in claim 1, wherein the clock signal is oversampled.

5. The method as claimed in claim 1, wherein the digital data signal is oversampled, or is sampled only at the sampling points, in order to obtain the data signal digital value sequence.

6. The method as claimed in claim 1, wherein the data signal digital value sequence is a binary value sequence.

7. The method as claimed in claim 6, wherein the digital value is formed from the data signal digital values, and wherein the data signal digital values form bits of the digital value.

8. The method as claimed in claim 1, further comprising sampling a frame signal in order to obtain a frame signal digital value sequence, wherein the digital value is formed using the frame signal digital value sequence as well as the data signal digital values.

9. The method as claimed in claim 1, wherein the clock signal and the digital data signal are output by an analog-digital converter with serial output.

10. A computing unit configured to carry out the method as claimed in claim 1.

11. The computing unit as claimed in claim 10, the computing unit being configured as an integrated circuit, in particular as a field programmable gate array (FPGA).

12. A microscope comprising the computing unit as claimed in claim 10.

* * * * *